US005688527A

United States Patent [19]

Bordier et al.

[11] Patent Number: 5,688,527

[45] Date of Patent: Nov. 18, 1997

[54] LYSINE DERIVATIVES, PROCESS OF PREPARATION, USES, AND COMPOSITIONS COMPRISING THEM

[75] Inventors: Thierry Bordier, Tremblay; Michel Philippe, Wissous, both of France

[73] Assignee: L'Oreal, Paris, France

[21] Appl. No.: 590,446

[22] Filed: Jan. 23, 1996

[30] Foreign Application Priority Data

Jan. 31, 1995 [FR] France .................................. 95 01112

[51] Int. Cl.[6] .......................... A61K 9/127; C07C 271/22

[52] U.S. Cl. ............................ 424/450; 424/69; 424/722

[58] Field of Search .............................. 424/450, 69, 722

[56] References Cited

FOREIGN PATENT DOCUMENTS 0336265 3/1989 European Pat. Off. .
0447287 2/1991 European Pat. Off. .
0545786 11/1992 European Pat. Off. .
0139481 9/1994 European Pat. Off. .

*Primary Examiner*—Paula K. Hutzell
*Assistant Examiner*—Benet Prickril
*Attorney, Agent, or Firm*—Finnegan, Henderson, Farabow, Garrett & Dunner, L.L.P.

[57] ABSTRACT

New lysine derivatives containing a fluoroalkyloxycarbonyl or fluoroalkylsulphonyl group of formula:

$$COOH—CH(NH_2)—(CH_2)_4—NH—X—(CH_2)_n—R$$

in which n ranges from 0 and 4, X represents a divalent COO or $SO_2$ group and R represents a linear or branched perfluoroalkyl radical having from 4 to 20 carbon atoms, salts thereof, and mixtures of the derivatives and the salts. A process for the preparation of these derivatives, salts, and mixtures and use of such derivatives, salts, and mixtures, especially in cosmetics. Compositions, especially cosmetic compositions, comprising the derivatives, salts, and mixtures.

39 Claims, No Drawings

LYSINE DERIVATIVES, PROCESS OF PREPARATION, USES, AND COMPOSITIONS COMPRISING THEM

The subject of the present invention is compounds containing a fluoroalkyloxycarbonyl or fluoroalkylsulphonyl group, which are derived from lysine, their process of preparation, their use, especially in cosmetics, and the compositions, especially cosmetic compositions, comprising them.

Compositions, especially cosmetic, pharmaceutical, or food compositions, are known which can be provided in the form of a powder, known as a compact powder, obtained by compacting. They are generally anhydrous compositions which may mainly be composed of solid particles and of a fatty binder, shaped by compression.

The development of such compositions raises, however, many difficulties because the final composition must be sufficiently homogeneous and compact to have a good ability to be removed and, moreover, to avoid fragmentation which may be caused, especially, by impacts.

A description is given, in Patent Application EP 139,481, of cosmetic compositions using, as agents for modifying the surface of inorganic compounds, for the purpose of increasing the dispersibility thereof, either a monoacylated derivative of a basic amino acid in which the aliphatic acyl group has 8–22 carbon atoms or an N,N-diacylated derivative of a basic amino acid in which the acyl groups, which are identical or different, have 1–22 carbon atoms.

A description is also given, in Patent Application EP 336,265, of cosmetic compositions for hair shaping comprising, as surface-active agents, an N-monoacylated derivative of a basic amino acid in which the acyl group has 8–22 carbon atoms.

However, it is observed that the acylated derivatives of the basic amino acids described previously are very difficult and even impossible to compact.

The aim of the present invention is to provide new compounds which make it possible to facilitate the preparation of such compositions, by satisfying the abovementioned requirements, without exhibiting the disadvantages of the prior art.

The subject of the present invention is therefore a lysine derivative containing an $N^{\varepsilon}$-fluoroalkyloxycarbonyl or $N^{\varepsilon}$-fluoroalkylsulphonyl group of formula (I):

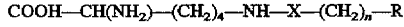

$$COOH—CH(NH_2)—(CH_2)_4—NH—X—(CH_2)_n—R$$

in which n ranges from 0 to 4, X represents a divalent COO or $SO_2$ group and R represents a linear or branched perfluoroalkyl radical having from 4 to 20 carbon atoms, the salts of the compounds of formula (I), their optical isomers of D or L configuration, and their mixtures.

Another subject of the invention is a composition, inter alia cosmetic, pharmaceutical, hygiene or food, comprising at least one derivative of formula (I).

A further subject of the invention is the use of at least one derivative of formula (I) as a substance for coating substrate particles. It has in fact been observed that the said particles, generally powders, once compacted, make possible good cohesion of the product, the result of which is a compacted product which does not easily disintegrate.

Moreover, it has been observed that the derivatives according to the invention also make it possible to confer particularly advantageous spreading, skin-adhesion and light-scattering qualities, as well as a pleasant and smooth feel and a better water resistance, probably due to the presence of the fluorinated chain, on the cosmetic composition comprising them.

More precisely, the subject of the invention is a lysine derivative of formula (I):

$$COOH—CH(NH_2)—(CH_2)_4—NH—X—(CH_2)_n—R$$

in which n ranges from 0 and 4, X represents a divalent COO or $SO_2$ group and R represents a linear or branched perfluoroalkyl radical having from 4 to 20 carbon atoms, the salts of the compounds of formula (I), their optical isomers of D or L configuration, and their mixtures.

Perfluoroalkyl radical is understood to mean a radical in which all the hydrogen atoms are replaced by fluorine atoms.

The R radical can preferably represent a linear or branched perfluoroalkyl radical having from 4 to 8 carbon atoms.

Mention may be made, among the derivatives according to the invention, of $N^{\varepsilon}$-2-(F-octyl)ethyloxycarbonyl-L-lysine and $N^{\varepsilon}$-2-(F-hexyl)ethyloxycarbonyl-L-lysine.

The salts of the derivatives of formula (I) can be chosen from the salts of monovalent inorganic cations, such as those of sodium, or divalent inorganic cations, such as those of zinc or of copper. The salts can also be chosen from the salts of organic cations, such as those of aminopropanediol, trishydroxyaminomethane, glucamine and N-methylglucamine.

The derivatives according to the invention can be provided in a solid form generally having a particle size ranging from 10 to 500,000 nm and preferably ranging from 100 to 25,000 nm.

These derivatives are generally insoluble in oils and in aqueous solutions in which the pH ranges from 5 to 8. They generally have a high melting point, greater than 200° C.

The composition according to the invention comprising the said lysine derivatives can be provided in various forms such as dispersions, optionally thickened or gelled lotions, optionally compacted powders, milks, creams, sticks, foams or sprays when it is packaged as an aerosol, oil-in-water or water-in-oil emulsions, liposomal dispersions or alternatively solid preparations.

The derivatives according to the invention can be included in the composition in a proportion generally ranging from 0.05% to 80% by weight, preferably in a proportion from 0.5 to 30% by weight, with respect to the total weight of the composition.

The derivatives according to the invention can be present in the composition in the free form and/or in the form of a combination with substrate particles which they coat.

In addition to the derivatives according to the invention, the composition can also comprise at least one additive chosen from surface-active agents, fatty substances, organic solvents, silicones, thickeners, emollients, sunscreen agents, treating agents, anti-foaming agents, moisturizing agents, fragrances, preservatives, anti-oxidizing agents, sequestrants, flavouring agents, basifying or acidifying agents, fillers and pigments.

Mention may be made, among the fatty substances which can be used in the composition according to the invention, of oils, waxes, fatty acids, fatty alcohols and/or their mixtures.

The oils and waxes can be of animal, vegetable, inorganic or synthetic origin. Mention may in particular be made of hydrogenated palm oil, hydrogenated castor oil, liquid petrolatum, liquid paraffin or purcellin oil.

Mention may also be made of beeswax, montan wax, carnauba wax, candelilla wax, sugar cane wax, Japan wax, ozocerite, microcrystalline waxes, paraffin wax, lanolin wax, hydrogenated lanolin wax and acetylated lanolin wax.

Mention may especially be made, among the particles which can be coated by the derivatives according to the invention, of pigments, particulate fillers and microspheres such as hollow vinylidene chloride/acrylonitrile copolymer microspheres.

Mention may more particularly be made, among the fillers, of optionally coloured insoluble fillers such as nanopigments of metal oxides, such as titanium, zinc, iron, manganese, caesium and/or zirconium oxides.

The composition according to the invention can be provided in the form of make-up compositions such as foundation creams, tinted creams, mascaras, blushers, eye shadows, lipsticks or nail varnishes.

According to a specific embodiment, the composition according to the invention can be provided in the so-called compact form, the derivative according to the invention facilitating compaction of the ingredients of the said compositions and especially the cohesion of the compacted product.

Mention may especially be made, among these compact compositions, of foundation creams, blushers, eye shadows and lipsticks.

The composition according to the invention can also be provided in the form of a pharmaceutical or hygiene composition, such as toothpastes, exfoliative compositions, powders for the body or for babies, and anti-perspirant powders, or indeed in the form of a food composition.

Another subject of the invention is a process for the preparation of a derivative of formula (I), comprising the steps of:

reacting, in aqueous medium and at basic pH, lysine, at least one of its salts, or a mixture of lysine and at least one of its salts, of known configuration, with a solution of a copper salt, reacting the solution of the copper complex with a compound of formula (11):

$$R—(CH_2)_n—X—Y$$

in which n ranges from 0 and 4, R and X are as defined above and Y is chosen from a chlorine atom, a chloromethyl radical and an imidazolyl radical, the said compound of formula (II) being added with or without solvent, to form a copper salt;

treating the copper salt of the substituted lysine obtained with a decomplexing agent and, optionally, purifying the lysine derivative, the salt, or the mixture obtained.

Mention may particularly be made, among the copper salt solutions used in the process according to the invention, of copper sulphate solutions.

The basic pH of the reaction medium preferably ranges from 8 to 14.

According to a preferred embodiment of the preparation process, the decomplexing agent used is an aqueous solution of the disodium salt of ethylenediaminetetra-acetic acid.

Examples of the preparation of lysine derivatives according to the invention, and an example of a composition comprising such a derivative, will now be given by way of illustration only and does not limit the invention in any way.

The preparation examples are obtained according to the following procedure:

10 g of L-lysine monohydrochloride are dissolved in 44 ml of a 10% aqueous sodium hydroxide solution in a 250 ml three-necked flask equipped with a thermometer and a 50 ml dropping funnel.

A solution of 6.8 g of copper sulphate pentahydrate in 40 ml of water is introduced into the reaction mixture.

4.6 g of sodium hydrogencarbonate are added to the homogeneous mixture, which has been cooled to a temperature of 5° C., followed by the dropwise addition of fluorinated alkyl chloroformate.

After stirring overnight at room temperature, the reaction mixture is filtered and the precipitate, corresponding to the final product in the form of a copper complex, is washed with water and with acetone and then dried in an oven under reduced pressure. To remove the copper, ×mol of complex are treated at reflux for 4 hours with a 10% aqueous solution of the dihydrated disodium salt of ethylene diaminetetraacetic acid. The treatment can be repeated several times in order to obtain an entirely decomplexed product.

EXAMPLE 1

Preparation of $N^\varepsilon$-2-(F-Octyl)Ethyloxycarbonyl-L-Lysine

By following the above procedure, 27 g (yield of 77%) of white product are obtained, heptadeca-fluorodecyl chloroformate being used as fluorinated alkyl chloroformate.

Chemical analysis gives the following characteristics:

Melting: T>260° C. (measured on a Kofler stage)

Mass spectrum: m/z 637 $(MH)^+$

Elemental analysis: ($C_{17}H_{17}F_{17}N_2O_4$, molecular weight: 636.309)

| | C | H | F | N |
|---|---|---|---|---|
| % calculated | 32.09 | 2.69 | 50.76 | 4.40 |
| % measured | 31.27 | 2.52 | 48.93 | 3.79 |

Particle size (measured using a Coulter Counter TA2): number (–average): 2.80 μm (standard deviation: 2.32 μm)

Optical rotation: $[\alpha]_D$=+4°, concentration c=1, solvent: $CH_3COOH$

EXAMPLE 2

Preparation of $N^\varepsilon$-2-(F-Hexyl)Ethyloxycarbonyl-L-Lysine

By following the above procedure, 23 g of a white product (yield of 77%) are obtained, tridecafiuorooctyl chloroformate being used.

Chemical analysis gives the following chemical characteristics:

Melting: T>260° C. (measured on a Kofler stage)

Mass spectrum: m/z=537 $(MH)^+$

Elemental analysis: ($C_{15}H_{17}F_{13}N_2O_4$; molecular weight: 536.293)

| | C | H | F | N | Cu |
|---|---|---|---|---|---|
| % calculated | 33.59 | 3.20 | 46.05 | 5.22 | |
| % measured | 32.67 | 2.99 | 45.05 | 4.53 | 67 ppm |

Particle size: (measured using a Coulter Counter TA2): number (–average): 3.21 μm (standard deviation: 2.95 μm)

Optical rotation: $[\alpha]_D$=+4°, concentration c=1, solvent: $CH_3COOH$

EXAMPLE 3

A compacted powder is prepared which has the following composition:

Composition A:

Talc 38.4 g

Bismuth oxychloride 10 g

Zinc stearate 4 g

Compound of Example 1 20 g

Nylon powder 20 g

Composition B:

Iron oxides 1.6 g

Liquid petrolatum 6 g

The powder is obtained in the following way: the composition A is ground in a grinder of Kenwood type for approximately 5 minutes with slow agitation. The composition B is added and the entire mixture is ground for approximately 2 minutes at the same speed and then for 3 minutes at a faster speed. The preparation is then sieved on a 0.16 mm sieve, and this mixture is then compacted in small dishes.

A compacted powder is obtained which exhibits good adhesion and which spreads readily and pleasantly on the skin, while being smooth to the touch.

Moreover, the presence of the compound of Example 1 prevents excessively easy disintegration of the compacted product.

We claim:

1. A lysine derivative of formula (1):

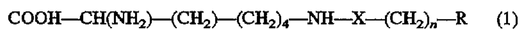

$$COOH—CH(NH_2)—(CH_2)—(CH_2)_4—NH—X—(CH_2)_n—R \quad (1)$$

in which n ranges from 0 to 4, X represents a divalent COO or $SO_2$ group and R represents a linear or branched perfluoroalkyl radical having from 4 to 20 carbon atoms or a salt of the lysine derivative of formula (1).

2. A derivative or salt according to claim 1, wherein said derivative or said salt is an optical isomer of D or L configuration.

3. A derivative or salt according to claim 1 wherein said perfluoroalkyl radical has from 4 to 8 carbon atoms.

4. A salt according to claim 1 wherein said salt is a salt of a monovalent inorganic cation, a divalent inorganic cation, or an organic cation.

5. A salt according to claim 4 wherein said monovalent inorganic cation is sodium.

6. A salt according to claim 4 wherein said divalent inorganic cation is zinc or copper.

7. A salt according to claim 4 wherein said organic cation is a cation of aminopropanediol, trishydroxyaminomethane, glucamine, or N-methylglucamine.

8. A derivative according to claim 1 wherein said derivative is $N^{\epsilon}$-2-(F-octyl)ethyloxycarbonyl-L-lysine or $N^{\epsilon}$-2-(F-hexyl)ethyloxycarbonyl-L-lysine.

9. A derivative or salt according to claim 1 wherein said derivative or said salt has a particle size ranging from 10 nm to 500,000 nm.

10. A derivative or salt according to claim 9 wherein said particle size ranges from 100 nm to 25,000 nm.

11. A composition comprising a derivative according to claim 1, a salt of said derivative or a mixture of said derivative and said salt in a physiologically and cosmetically acceptable carrier.

12. A composition according to claim 11, wherein said composition is a dispersion, an optionally thickened or gelled lotion, an optionally compacted powder, a milk, a cream, a stick, a foam, a spray, an oil-in-water emulsion, a water-in-oil emulsion, or a liposomal dispersion.

13. A composition according to claim 11 wherein said derivative, said salt, or said mixture ranges from 0.05% to 80% by weight with respect to the total weight of the composition.

14. A composition according to claim 13 wherein said derivative, said salt, or said mixture ranges from 0.5% to 30% by weight with respect to the total weight of the composition.

15. A composition according to claim 11 wherein said derivative, said salt, or said mixture is in the free form, is in the form of a combination with substrate particles coated by said derivative, said salt, or said mixture, or is in the form of a mixture of said free form and said combination.

16. A composition according to claim 15 wherein said substrate particles are pigments, particulate fillers or microspheres.

17. A composition according to claim 16 wherein said microspheres are hollow vinylidene chloride/acrylonitrile copolymer microspheres.

18. A composition according to claim 11 further comprising at least one additive, wherein said at least one additive is a surface-active agent, a fatty substance, an organic solvent, a silicone, a thickener, an emollient, a sunscreen agent, a treating agent, an anti-foaming agent, a moisturizing agent, a fragrance, a preservative, an anti-oxidizing agent, a sequestrant, a flavoring agent, a basifying agent, an acidifying agent, a filler or a pigment.

19. A composition according to claim 18 wherein said fatty substance is an oil, a wax, a fatty acid or a fatty alcohol.

20. A composition according to claim 19 wherein said oil is of animal, vegetable, inorganic, or synthetic origin.

21. A composition according to claim 20 wherein said oil is hydrogenated palm oil, hydrogenated castor oil, liquid petrolatum, liquid paraffin or purcellin oil.

22. A composition according to claim 19 wherein said wax is of animal, vegetable, inorganic or synthetic origin.

23. A composition according to claim 22 wherein said wax is beeswax, montan wax, carnauba wax, candelilla wax, sugar cane wax, Japan wax, ozocerite, microcrystalline waxes, paraffin wax, lanolin wax, hydrogenated lanolin wax or acetylated lanolin wax.

24. A composition according to claim 16 wherein said particulate fillers are optionally coloured insoluble fillers.

25. A composition according to claim 24 wherein said optionally colored insoluble fillers are nanopigments of metal oxides.

26. A composition according to claim 25 wherein said nanopigments of metal oxides are titanium, zinc, iron, manganese, caesium or zirconium oxides.

27. A composition according to claim 11 wherein said composition is in the form of a make-up composition.

28. A composition according to claim 27, wherein said make-up composition is a foundation cream, a tinted cream, a mascara, a blusher, an eye shadow, a lipstick or a nail varnish.

29. A composition according to claim 27, wherein said make-up composition is in the compact form.

30. A composition according to claim 29, wherein said make-up composition is a foundation cream, blusher, an eye shadow or a lipstick.

31. A composition according to claim 11, wherein said composition is a cosmetic composition, a pharmaceutical composition, a hygiene composition or a food composition.

32. A composition according to claim 31, wherein said composition is a toothpaste, an exfoliative composition, a skin-care composition, a body powder, or an anti-perspirant.

33. A process for the preparation of a lysine derivative according to claim 1, a salt of said lysine derivative or a mixture of said derivative and said salt, said process comprising:

reacting lysine, at least one salt of lysine or a mixture of lysine and at least one of said salts in an aqueous medium and a basic pH, with a copper salt solution to form a copper complex solution;

reacting said solution of the copper complex with a compound of the formula:

$$R-(CH_2)_n-X-Y$$

in which n ranges from 0 to 4, R and X are defined as in claim 1 and Y is a chlorine atom, a chloromethyl radical or an imidazolyl radical to obtain a copper salt;

treating said copper salt with a decomplexing agent to obtain said derivative, said salt or said mixture; and optionally purifying said derivative, said salt or said mixture.

34. A process according to claim 33 wherein said copper salt solution is copper sulphate solution.

35. A process according to claim 33 wherein said decomplexing agent is an aqueous solution of the disodium salt of ethlenediaminetetra-acetic acid.

36. A method of coating a substrate particle comprising coating a substrate particle with said derivative or said salt according to claim 1, or with a mixture of said derivative and said salt.

37. A method for facilitating compaction of compositions including particles, said method comprising the step of including in a composition a derivative or a salt according to claim 1, or a mixture of said derivative and said salt, either as particles or as a coating on substrate particles, wherein said coated substrate particles are included in said composition; and thereafter compacting said composition.

38. A mixture of (a) lysine derivatives according to claim 1, (b) salts of said derivatives, or (c) at least one of said lysine derivatives and at least one salt of said derivatives.

39. A composition comprising (a) lysine derivatives according to claim 1, (b) salts of said derivatives, or (c) at least one of said lysine derivatives and at least one salt of said derivatives, together with a physiologically and cosmetically acceptable carrier.

* * * * *

UNITED STATES PATENT AND TRADEMARK OFFICE

CERTIFICATE OF CORRECTION

PATENT NO. : 5,688,527

DATED : November 18, 1997

INVENTOR(S) : Theirry BORDIER and Michel PHILIPPE

It is certified that error appears in the above-identified patent and that said Letters Patent is hereby corrected as shown below:

Col. 1, line 43, change "$N^C$" to --$N^ε$-- .

Col. 1, line 44, change "$N^C$" to --$N^ε$-- .

Col. 2, line 15, change "$N^C$" to --$N^ε$-- .

Col. 2, line 16, change "$N^C$" to --$N^ε$-- .

Col. 4, line 15, change "$N^C$" to --$N^ε$-- .

Col. 4, line 40, change "$N^C$" to --$N^ε$-- .

Claim 8, col. 5, line 52, change "$N^C$" to --$N^ε$-- (both occurrences).

Claim 11, col. 5, line 62, after "derivative" insert --,--.

Signed and Sealed this

Seventeenth Day of February, 1998

Attest:

BRUCE LEHMAN

*Attesting Officer*

*Commissioner of Patents and Trademarks*